Figure 1:
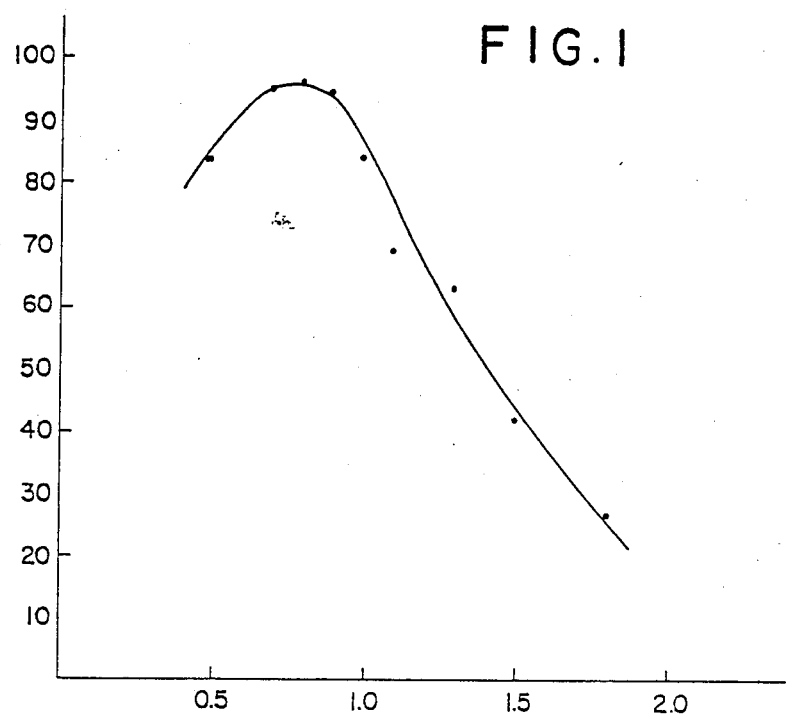
Figure 2A:
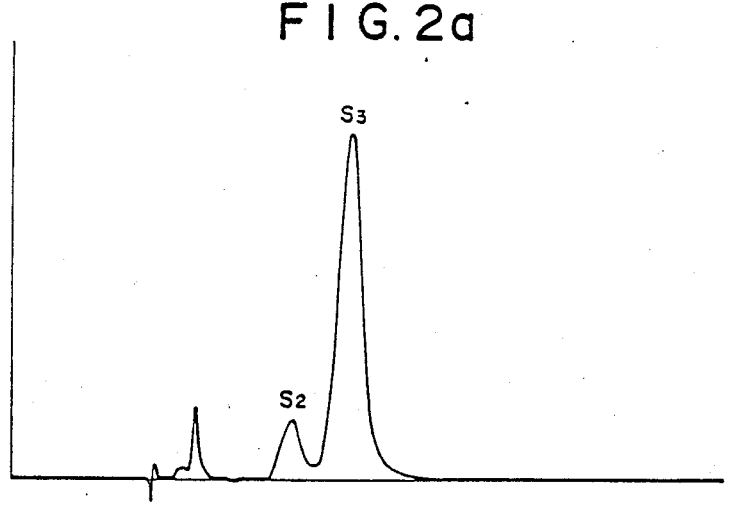
Figure 2B:
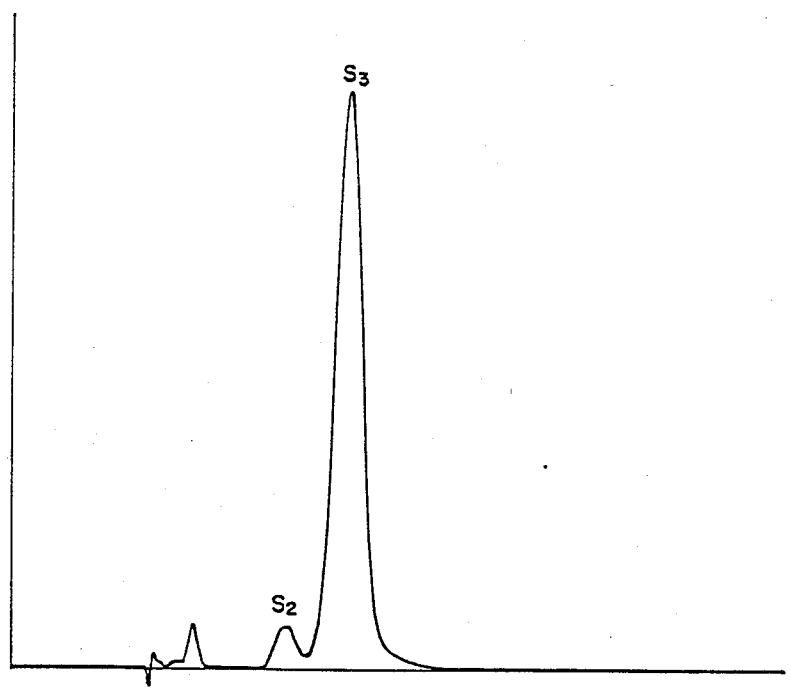
Figure 2C:
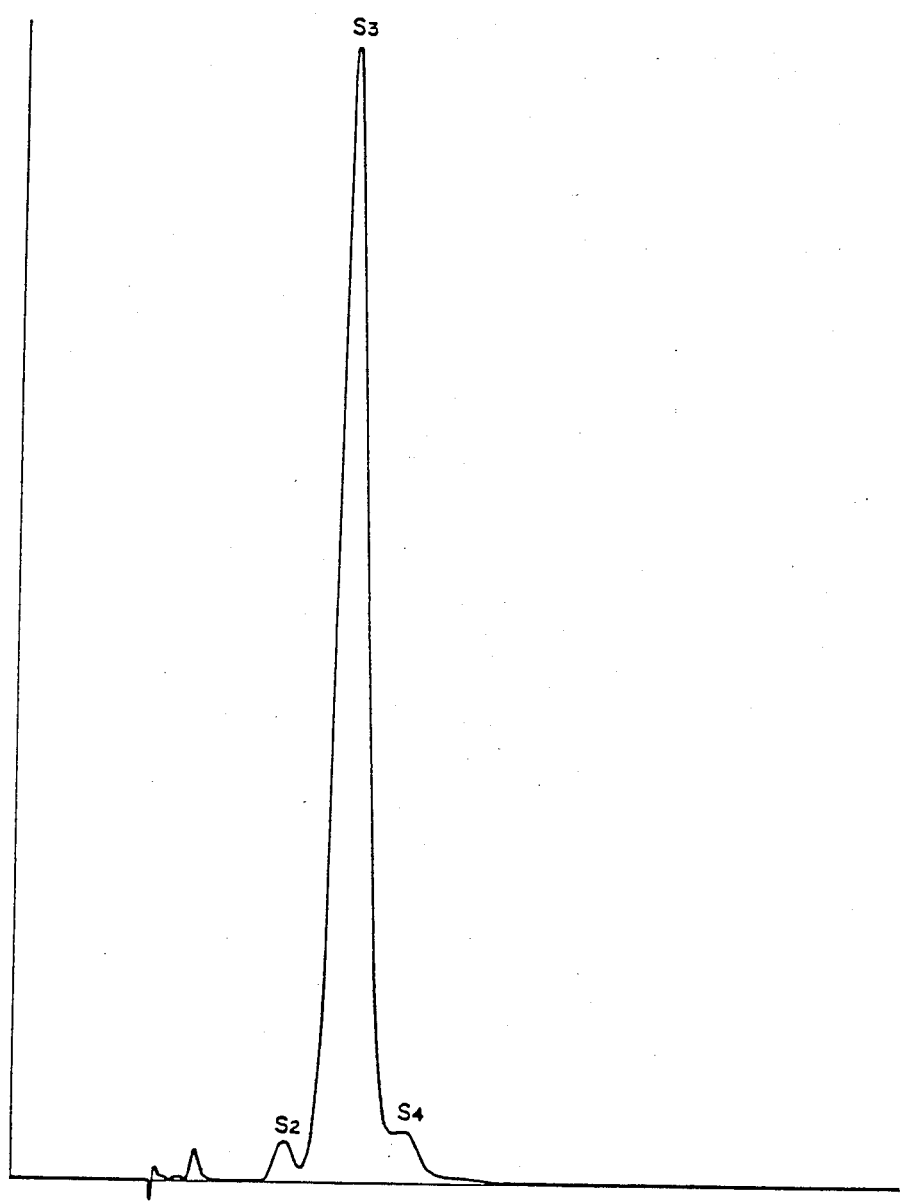
Figure 2D:
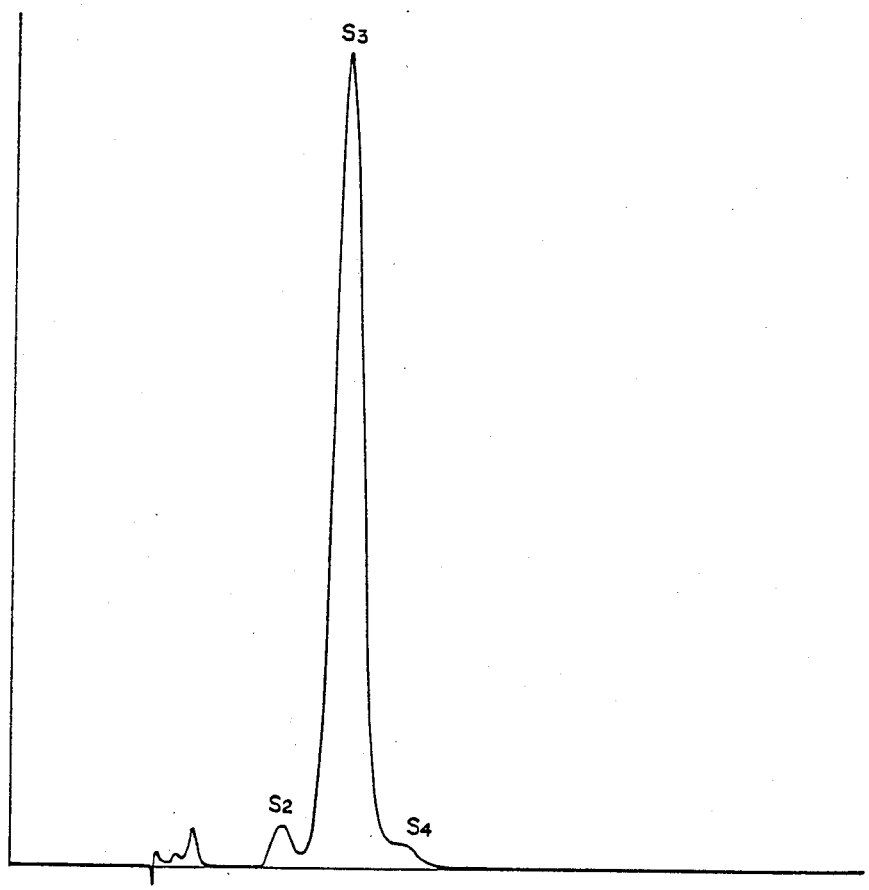
Figure 2E:
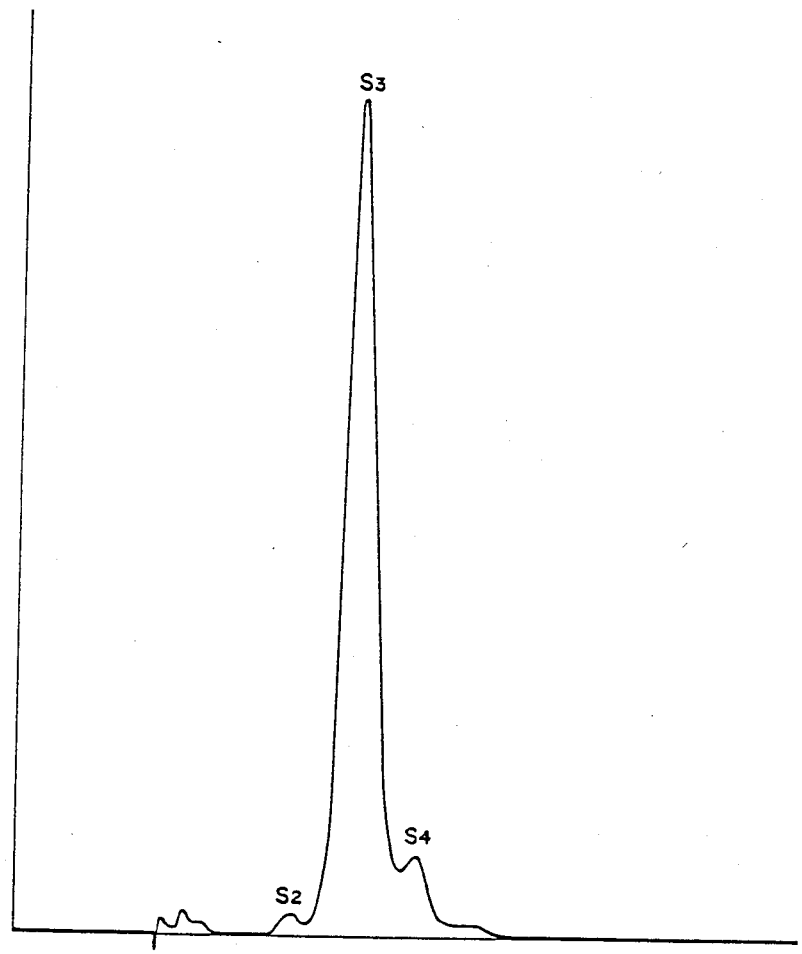
Figure 2F:
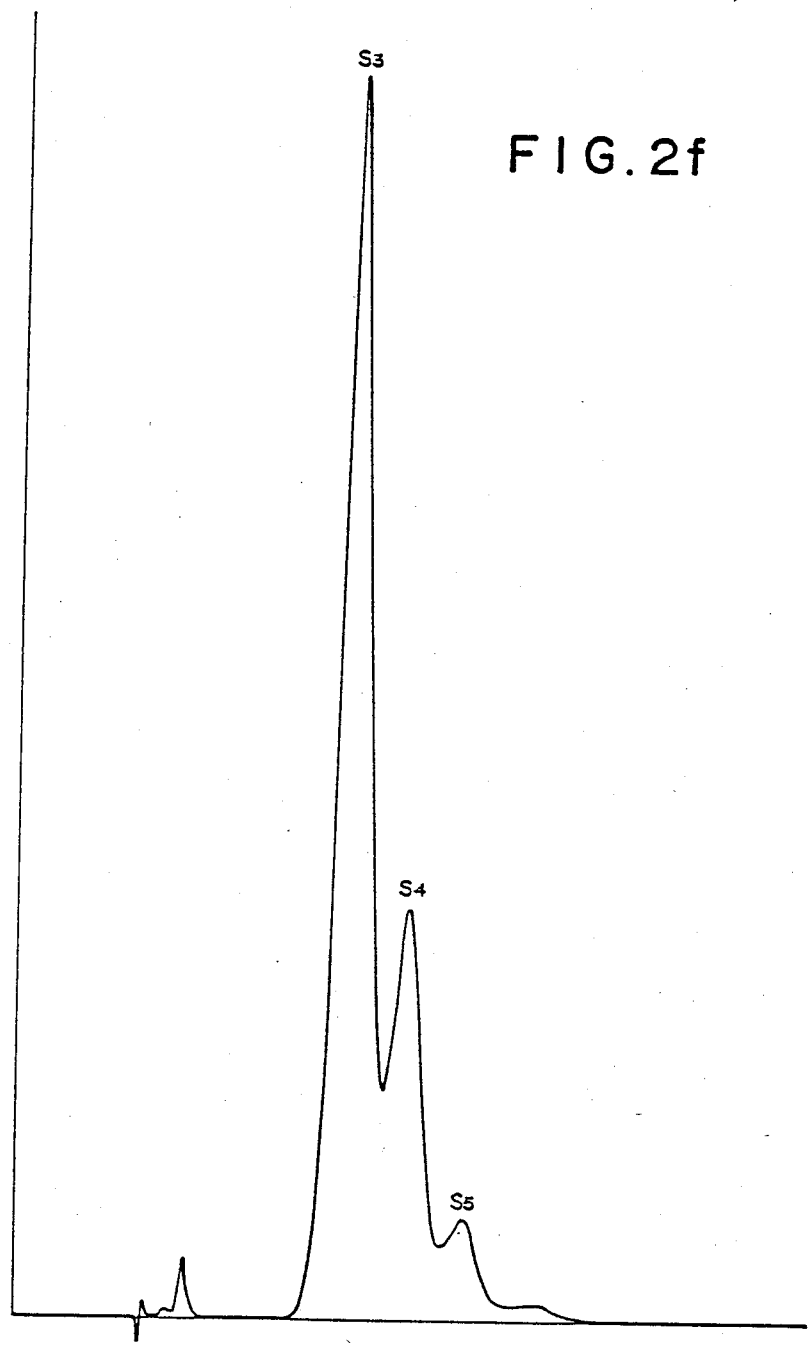
Figure 2G:
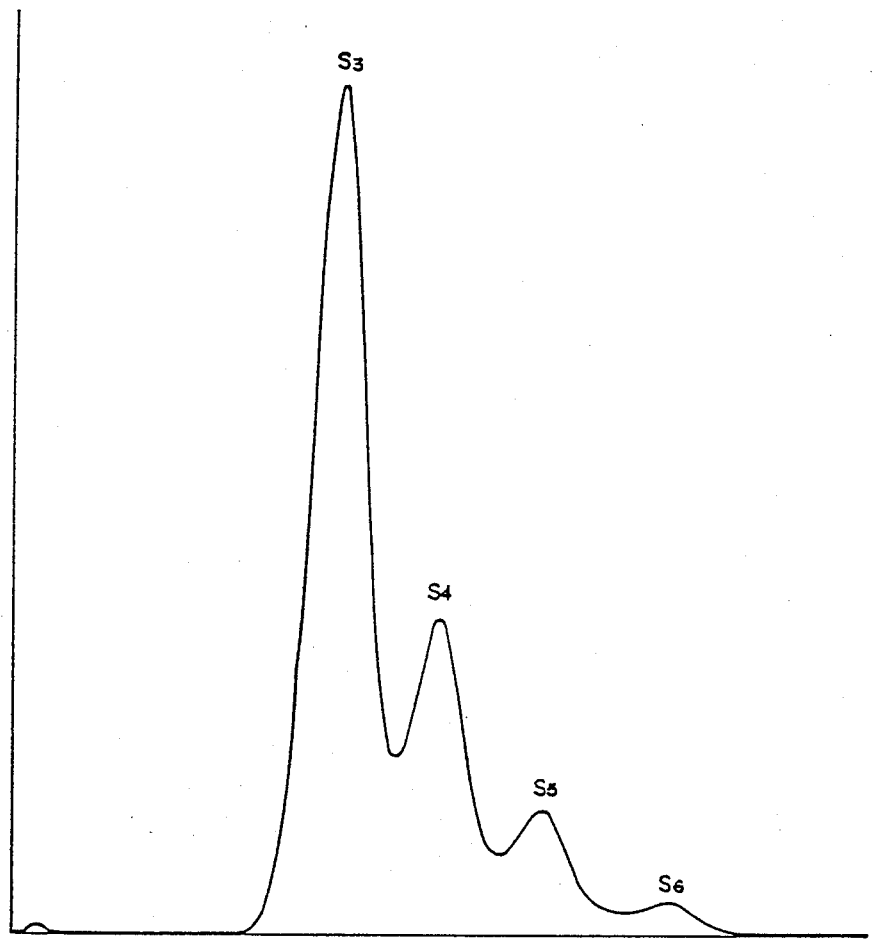

United States Patent [19]

Koyama et al.

[11] Patent Number: 4,564,709

[45] Date of Patent: Jan. 14, 1986

[54] PROCESS FOR THE PRODUCTION OF DIALKYL-TRISULFIDES

[75] Inventors: Yuichiro Koyama, Yokohama; Hiroshi Nakazawa, Nagano; Toshiaki Yamashita, Myoko; Hitoshi Moriyama, Jyoetsu, all of Japan

[73] Assignee: Pennwalt Corporation, Philadelphia, Pa.

[21] Appl. No.: 545,392

[22] PCT Filed: Feb. 12, 1983

[86] PCT No.: PCT/JP83/00042

§ 371 Date: Oct. 7, 1983

§ 102(e) Date: Oct. 7, 1983

[87] PCT Pub. No.: WO83/02273

PCT Pub. Date: Aug. 18, 1983

[30] Foreign Application Priority Data

Feb. 13, 1982 [JP] Japan .................................. 57-21492

[51] Int. Cl.$^4$ .................. C07C 149/12; C07C 148/00
[52] U.S. Cl. ........................................ 568/26; 568/21
[58] Field of Search ..................... 568/26, 21

[56] References Cited

U.S. PATENT DOCUMENTS

| 3,022,351 | 2/1962 | Mihm et al. | 568/26 |
| 3,275,693 | 9/1966 | Bapsères et al. | 568/26 |
| 3,308,166 | 3/1967 | Biensan et al. | 568/26 |
| 3,392,201 | 7/1968 | Warner | 568/26 |

FOREIGN PATENT DOCUMENTS

1162334  8/1969  United Kingdom ............... 568/26

*Primary Examiner*—George F. Lesmes
*Assistant Examiner*—S. A. Gibson
*Attorney, Agent, or Firm*—Wegner & Bretschneider

[57] ABSTRACT

Dialkyl-trisulfides having a minimum grade of copper-strip corrosivity which are suitable as extreme-pressure additives, are produced at high selectivity by reacting alkyl-mercaptans and sulfur at a quantitative ratio in a range of 0.5 to 1.0 gram atom of sulfur to 1 mol of alkyl-mercaptan in the presence of magnesium oxide as catalyst.

9 Claims, 10 Drawing Figures

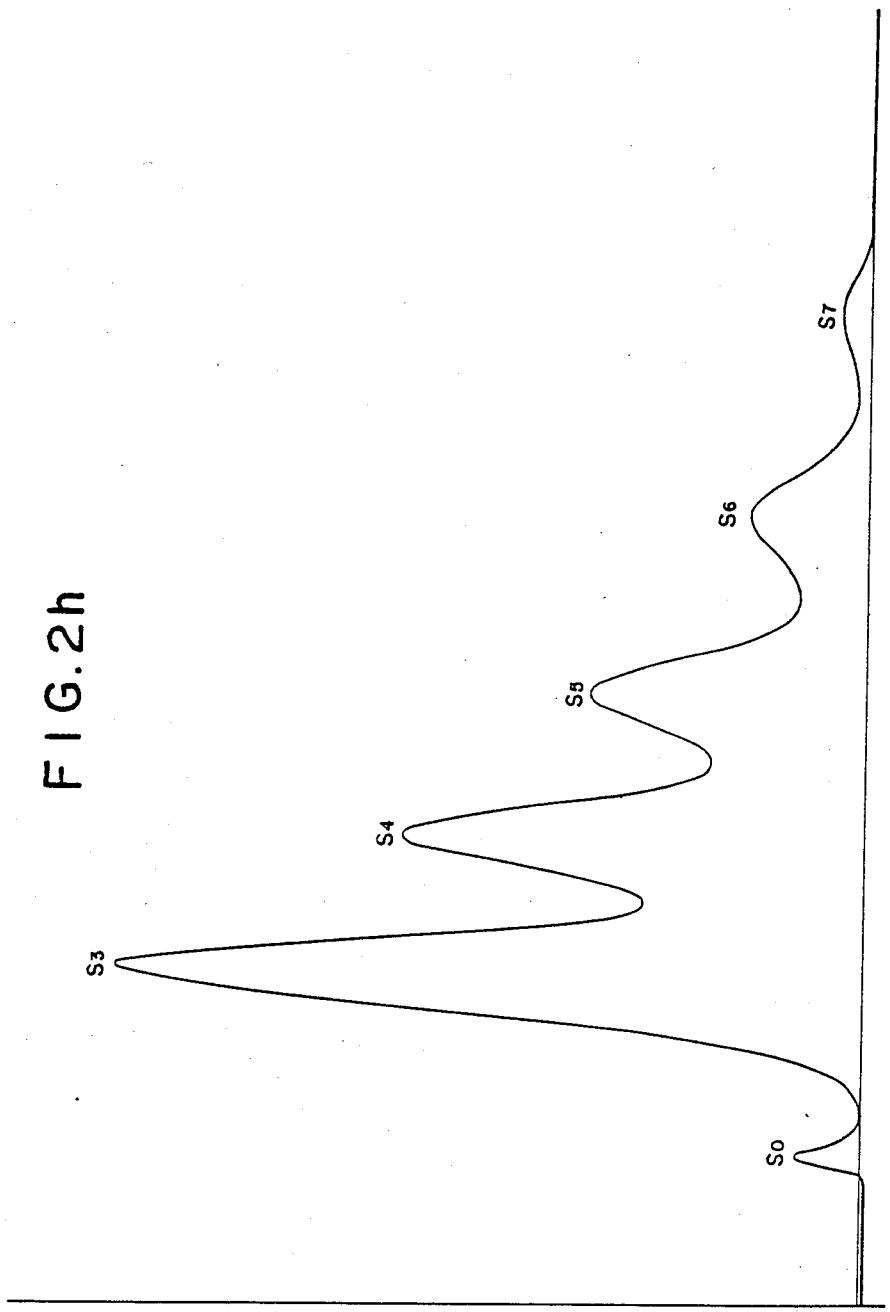

PROCESS FOR THE PRODUCTION OF DIALKYL-TRISULFIDES

THE FIELD OF THE TECHNOLOGY

The present invention relates to a process for the production of dialkyltrisulfides; more specifically the invention concerns a method for the selective synthesis of dialkyl-trisulfides.

Dialkyl-polysulfides, such as ditertiarybutyl-polysulfide, ditertiarynonyl-polysulfide, ditertiarydodecyl-polysulfide and the like, have an excellent extreme-pressure efficacy, and are used as extreme-pressure additives to lubricating oils.

Among them dialkyl-polysulfides, dialkyl-trisulfides such as ditertiarybutyl-trisulfide, ditertiarynonyl-trisulfide, ditertiarydodecyl-trisulfide and the like have a minimum grade of copper-strip corrosivity specified under Japan Industrial Standard JIS.K-2513 "Testing Method for Copper Corrosion of Petroleum Products" and are exceedingly useful extreme-pressure additives.

BACKGROUND OF THE TECHNOLOGY

A process for the production of dialkyl-polysulfides is disclosed by U.S. Pat. No. 3,022,351, according to which dialkyl-polysulfides are obtained as a mixture of dissolved sulfur, dialkyl-disulfides, dialkyl-trisulfides, dialkyl-tetrasulfides, dialkyl-pentasulfides and dialkyl-hexasulfides by reacting alkyl-mercaptans and sulfur in the presence of oxides, hydroxides, alcoholates or sulfides of alkali metals or alkaline earth metals or amines as a catalyst and alcohols as an auxiliary catalyst.

Dialkyl-polysulfides obtained by said process contain highly copper-strip corrosive components such as dissolved sulfur, dialkyl-tetrasulfides, dialkyl-pentasulfides, dialkyl-hexasulfides and the like at considerably high contents, and it is excessively difficult to separate purely dialkyl-trisulfides, which have a minimum grade of said copper-strip corrosivity, from said dialkylpolysulfides.

As a classical process for the production of dialkyl-trisulfides, a process is known in which alkyl-mercaptans are reacted with sulfur dichloride in accordance with the following reaction equation (1).

$$2\text{-RSH} + \text{SCl}_2 \rightarrow \text{RS}_3\text{R} + 2\text{HCl} \qquad (1)$$

However, sulfur dichloride (SCl$_2$) is existing under equilibrium with sulfur monochloride as shown in the following reaction equation (2). Accordingly, sulfur dichloride always contains approximately 10% of sulfur monochloride (S$_2$Cl$_2$).

$$2\text{SCl}_2 \rightleftharpoons \text{S}_2\text{Cl}_2 + \text{Cl}_2 \qquad (2)$$

For this reason, the sulfur monochloride also reacts with alkyl-mercaptans to produce dialkyl-tetrasulfides as shown in the following reaction equation (3).

$$2\text{RSH} + \text{S}_2\text{Cl}_2 \rightleftharpoons \text{RS}_4\text{R} + 2\text{HCl} \qquad (3)$$

Thus, dialkyl-tetrasulfides, which are highly copper-strip corrosive, are contained in the reaction mixture obtained through the classical process. In order to isolate dialkyl-trisulfides from the reaction mixture, it is necessary to distill out dialkyl-trisulfides by using high-vacuum distillation equipment. Moreover, during the distillation, sulfur by-produced by decomposition of the bottom liquid at the distillation column is sublimated and easily mixes and dissolves into the products of dialkyl-trisulfides. Therefore, the above process has a defect to increase the copper-strip corrosivity of the products dialkyl-trisulfides.

As a process for selectively preparing dialkyl-trisulfides, the process is reported on J. Org. Chem. Vol. 32, page 3833 (1967) and J. Org. Chem. Vol. 31, page 601 (1966) by B. D. Vineyard, wherein the products dialkyl-trisulfides are obtained as a distillate after n-butylamine and alcohol are distilled off at a reduced pressure distillation of a reaction mixture obtained from the reaction of alkyl-mercaptans and sulfur in alcoholic solvent in the presence of n-butylamine as catalyst. However, this process also has the same defect as shown in the case of the classical process using sulfur dichloride, because the produced dialkyl-trisulfides are obtained as a distillate. Therefore, it cannot be employed as an industrial manufacturing process of dialkyl-trisulfides.

It is an object of the present invention to provide a process for the selective production of dialkyl-trisulfides employable as an industrial manufacturing process.

Inventors had eagerly researched to achieve the above object. As a result, they found that the reaction to produce dialkyl-polysulfides proceeds with stoichiometrically and dialkyl-polysulfides are synthesized at high yield by reacting alkyl-mercaptans and sulfur in the presence of magnesium oxide catalyst even without adding alcohols (as auxiliary catalysts), and further found that the selectivity to produce dialkyl-trisulfides in the dialkyl-polysulfides changes over a wide range by changing the quantity of sulfur at gram atom ratio against alkyl-mercaptans (mol), hence they had completed this invention.

DISCLOSURE OF THE INVENTION

The present invention is a process for the selective production of dialkyl-trisulfides, wherein alkyl-mercaptans and sulfur are reacted at a quantitative ratio in a range of 0.5 gram atom to 1.0 gram atom of sulfur to 1 mol of alkylmercaptans in the presence of magnesium oxide catalyst.

In the invention, dialkyl-trisulfides are those having straight or branched alkyl group of 3 to 18 carbon atoms, and ditertiarybutyl-trisulfide, ditertiarynonyl-trisulfide, ditertiarydodecyl-trisulfide etc. are particularly useful as extreme-pressure additives. Alkyl-mercaptans used as raw materials are those having straight or branched alkyl group of 3 to 18 carbon atoms corresponding to the objective dialkyl-trisulfides, for example, tertiarybutylmercaptan, tertiarynonyl-mercaptan, tertiarydodecyl-mercaptan etc. Sulfur used as another raw material is usually powder or crushed solid sulfur, but molten sulfur can be used too. The catalyst is magnesium oxide, and its powder of 200 mesh-pass is used in an amount corresponding to 0.1 to 3% by weight of alkyl-mercaptans.

In the invention, dialkyl-trisulfides are synthesized at a high selectivity by reacting alkyl-mercaptans and sulfur at a quantitative ratio of 1 mole to 0.5–1.0 gram atom in the presence of magnesium oxide at a temperature from 30° C. to 100° C. for 0.5 hour to 2 hours under stirring. Then, a highly pure dialkyl-trisulfides are obtained as a bottom liquid of distillation vessel by concentrating the filtrate after removal of magnesium oxide catalyst from the reaction mixture through usual distillation for removing unreacted mercaptans.

BRIEF EXPLANATION OF DRAWINGS (1) FIG. 1 A curve showing the selectivity of ditertiarynonyl-trisulfide in the filtrate of the reaction mixture in Example 1
Axis of ordinate: Selectivity (%) of ditertiarynonyl-trisulfide
Axis of abscissa: Quantitative ratio (sulfur gram atom to one mol of tertiarynonyl-mercaptan)

(2) FIG. 2 (a)-(h) Analytical curve by high-speed liquid chromatography of the filtrate of the reaction mixture in Example 1
$S_0$: Peak of unreacted sulfur dissolved in the filtrate
$S_2$: Peak of ditertiarynonyl-disulfide
$S_3$: Peak of ditertiarynonyl-trisulfide
$S_4$: Peak of ditertiarynonyl-tetrasulfide
$S_5$: Peak of ditertiarynonyl-pentasulfide
$S_6$: Peak of ditertiarynonyl-hexasulfide (3) FIG. 3 Copper-strip corrosion curve of dialkyl-trisulfide obtained in Example 1
Axis of ordinate: Degree of color change in copper-strip corrosion
Axis of abscissa: Quantitative ratio (sulfur gram atom to one mol of tertiarynonyl-mercaptan)

OPTIMUM MODE OF THE WORKING OF THE INVENTION

In the invention, the reaction proceeds almost stoichiometrically by using magnesium oxide catalyst in a quantity corresponding to 0.1 to 3% by weight of alkyl-mercaptans. If the quantity of the catalyst comes less than 0.1% by weight of alkyl-mercaptan, the reaction yield goes down, and where the quantity of the catalyst exceeds 3% by weight of alkyl-mercaptans, any significant improvement of the reaction yield does not appear. All other alkaline earth metal oxides than magnesium oxide, such as calcium oxide and barium oxide, can exhibit high catalytic activity attaining a reaction yield of 90% or more when they are used in combination with alcohols, for example, isopropyl alcohol butyl alcohol or the like, but if one of them is used singly, it exhibits very low catalytic activity merely obtaining a reaction yield of several percent or less.

Figure 3:
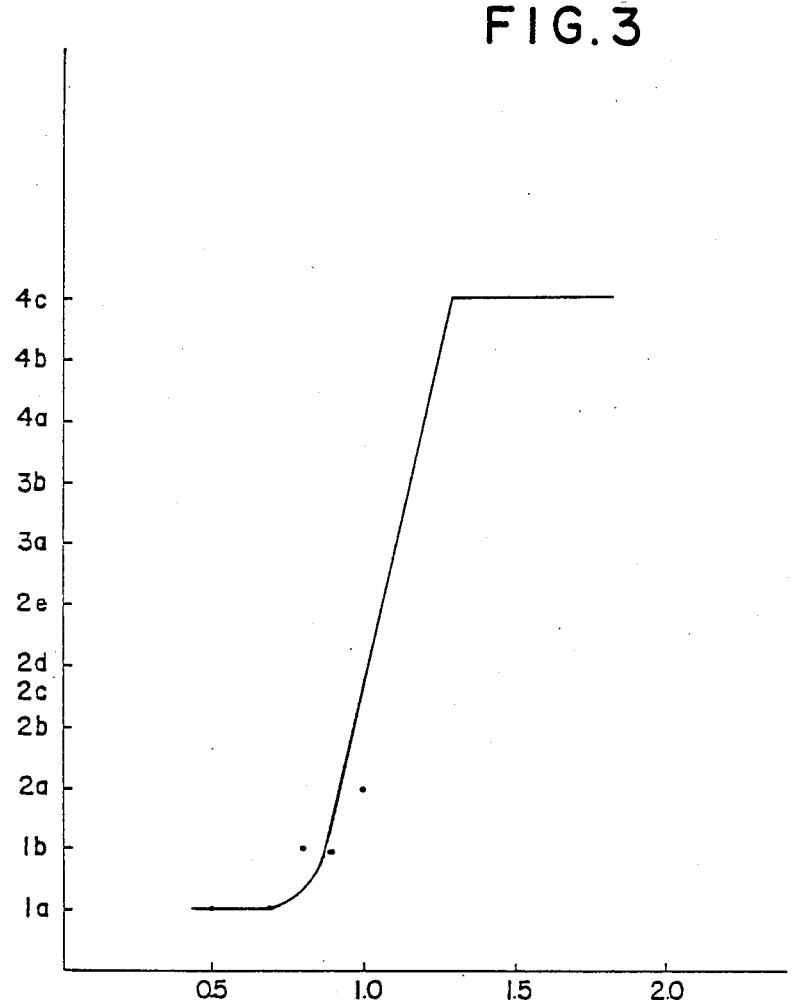

In the invention, sulfur and alkyl-mercaptans are reacted at a ratio from 0.5 gram atom to 1.0 gram atom of sulfur to 1 mol of alkyl-mercaptans, and more desirably 0.6 to 0.95 gram atom of sulfur and most desirably 0.6 to 0.8 gram atom of sulfur per 1 mol of alkyl-mercaptan. As shown in FIG. 2 attached hereto, if the ratio of sulfur gram atom to a mol of alkyl-mercaptan comes smaller, dialkyl-disulfides are by-produced, and if such ratio becomes too big dialkyl-tetrasulfide and higher dialkyl polysulfides emerge as by-products. As shown in FIG. 1, the selectivity of dialkyl-trisulfides is at a high level, when the ratio of sulfur gram atom to 1 mol of alkyl-mercaptans is in a range of 0.5 to 1.0 gram atom, particularly, in a range of 0.6 to 0.95 gram atom. Further, as shown in FIG. 3, the dialkyl-trisulfides obtained by using the ratio within the range of 0.6 to 0.8 gram atom have an excellent copper-strip corrosivity.

This invention is explained more precisely in the following examples. The scope of the invention, however, is in no way limited by the examples given below.

EXAMPLE 1

480 g (3 mols) of tertiarynonyl-mercaptan (TNM), 8.4 g of magnesium oxide powder were fed to a stirrer-mounted reaction vessel, and then various quanties of sulfur powder were added for each experiment of the reaction to change the ratio of sulfur atoms to 1 mol of tertiarynonyl-mercaptan. Those contents in the reactor were then externally heated to 70° C. under stirring and kept at said temperature for 30 minutes. Magnesium oxide in the reaction mixture was filtered off and the filtrate was then heated under reduced pressure to distil off unreacted tertiarynonyl-mercaptan, by-product hydrogen sulfide and other volatile components. As a consequence, a light-yellow, transparent, residual liquid was obtained. The liquid residue was then analyzed by a high-speed liquid chromatography (column: fine pak SIL 18, carrier: isopropanol/methanol: 5/95 V/V, flowrate: 0.7 ml/min, detector: UV abs at 226 nm).

Table 1 shows the ratio of sulfur gram atom to tertiarynonyl-mercaptan (mol), yield of residual liquid and the analytical results. FIG. 1 shows the selectivity of ditertiarynonyl-trisulfide. FIG. 2 shows an analytical curve obtained by high-speed liquid chromatography.

Further, a copper-strip corrosion test was conducted in compliance with the Japan Industrial Standard JIS.K-2513 "Testing Method for Copper Corrosion of Petroleum Products." Each of the residual liquids was added to spindle oil, the quantity of the added liquid was 5 percent by weight of the spindle oil. A well-polished copper strip was then submerged in the spindle oil mixture and then it was kept for 3 hours at 100° C., the strip was withdrawn to check the degree of color change. FIG. 3 shows the test results.

TABLE 1

| Symbol | $\frac{S(\text{gram-atom})}{TNM(\text{mol})}$ ratio | Yield of resid-liquid (g) | $S_0$ | $-S_2-$ | $-S_3-$ | $-S_4-$ | $-S_5-$ | $-S_6-$ | $-S_7-$ | $-S_8-$ |
|---|---|---|---|---|---|---|---|---|---|---|
| a | 0.5 | 275 | — | 16.1 | 83.9 | — | — | — | — | — |
| b | 0.7 | 362 | — | 5.2 | 94.8 | — | — | — | — | — |
| c | 0.8 | 405 | — | 3.4 | 96.2 | — | — | — | — | — |
| d | 0.9 | | — | 2.4 | 94.1 | 3.5 | — | — | — | — |
| e | 1.0 | 504 | — | 3.1 | 84.4 | 8.3 | 4.1 | — | — | — |
| f | 1.1 | | — | — | 68.7 | 23.3 | 6.2 | 1.3 | 0.3 | — |
| g | 1.3 | 540 | — | — | 63.1 | 23.2 | 10.3 | 3.2 | 0.2 | — |
| h | 1.5 | | 1.1 | — | 42.2 | 27.0 | 18.6 | 9.0 | 2.1 | — |
| i | 1.8 | | 2.6 | — | 26.5 | 27.9 | 22.5 | 13.6 | 6.0 | 1.1 |

EXAMPLE 2

To the same reaction vessels as used in Example 1, 606 g (3 mols) of tertiarydodecyl-mercaptan (TDM), 8.4 g of magnesium oxide powder and 67.2 g (2.1 gram-atom) of sulfur powder were fed. They were treated through the same procedures as shown in Example 1. Consequently, 443 g of a light-yellow, transparent residual liquid was obtained. The analytical results of the residual liquid by high-speed liquid chromatography showed 4.6% of ditertiarydodecyl-disulfide and 94.5% of ditertiarydodecyl-trisulfide. The copper-strip corrosion test (spindle oil; 5% residue addition; 100° C., 3 hours) under JIS.K-2513 of the liquid showed 1a (best) of the degree of color change.

COMMERCIAL FEASIBILITY

In the invention, dialkyl-trisulfides are selectively produced by using magnesium oxide as catalyst and limiting quantitative ratio of sulfur (gram atom) to alkyl-mercaptans (mol) in a range from 0.5 to 1.0. In addition, the dialkyl-trisulfides thus obtained have a minimum grade of copper-strip corrosivity and excel as the extreme-pressure additives to lubricating oils.

The present invention provides a process for the selective production of dialkyl-trisulfides suitable to the extreme-pressure additives to lubricating oils, and is of a large commercial significance to the industry.

We claim:

1. A process for the selective production of dialkyl trisulfides which consists essentially of reacting sulfur and an alkyl mercaptan at a quantitative ratio in the range of 0.5 gram atom to 1.0 gram atom of sulfur to 1 mol of alkyl mercaptan in the presence of magnesium oxide in an amount of 0.1 to 3 percent by weight of said alkylmercaptan and carried out at a temperature in the range of 30° C.–100° C.

2. The process of claim 1 wherein said alkyl mercaptan contains a straight or branched chain alkyl group of 3 to 18 carbon atoms.

3. The process of claim 2 wherein said alkyl mercaptan is tertiarynonyl mercaptan or tertiarydodecyl mercaptan.

4. The process of claim 1 carried out for 0.5 to 2 hours under stirring.

5. The process of claim 3 carried out for 0.5 to 2 hours under stirring.

6. The process of claim 1 wherein said sulfur is present in a range of 0.6 to 0.95 gram atom per mol of alkyl mercaptan.

7. The process of claim 6 wherein said sulfur is present in a range of 0.6 to 0.8 gram per mol of alkyl mercaptan.

8. The process of claim 3 wherein said sulfur is present in a range of 0.6 to 0.95 gram atom per mol of alkyl mercaptan.

9. The process of claim 8 wherein said sulfur is present in a range of 0.6 to 0.8 gram atom per mol of alkyl mercaptan.

* * * * *